US010939976B2

(12) United States Patent
Chan et al.

(10) Patent No.: US 10,939,976 B2
(45) Date of Patent: Mar. 9, 2021

(54) MINIMALLY INVASIVE INSTRUMENT WITH INSTANT FORCE FEEDBACK FUNCTION

(71) Applicant: Show-Chwan Memorial Hospital, Changhua (TW)

(72) Inventors: Shih-Chi Chan, Lukang Township, Changhua County (TW); Kai-Che Liu, Lukang Township, Changhua County (TW); Shih-Wei Huang, Lukang Township, Changhua County (TW); Hsien-Yeh Chen, Taipei (TW); Tien-Li Chang, Taipei (TW)

(73) Assignee: Show-Chwan Memorial Hospital, Changhua (TW)

( * ) Notice: Subject to any disclaimer, the term of this patent is extended or adjusted under 35 U.S.C. 154(b) by 373 days.

(21) Appl. No.: 15/987,237

(22) Filed: May 23, 2018

(65) Prior Publication Data
US 2019/0021808 A1  Jan. 24, 2019

(30) Foreign Application Priority Data
Jul. 24, 2017  (TW) .................................. 106124800

(51) Int. Cl.
*A61B 90/00* (2016.01)
*A61B 34/30* (2016.01)
(Continued)

(52) U.S. Cl.
CPC ........ *A61B 90/06* (2016.02); *A61B 17/00234* (2013.01); *A61B 34/30* (2016.02); *A61B 34/76* (2016.02); *G01L 5/226* (2013.01); *A61B 17/0469* (2013.01); *A61B 17/34* (2013.01); *A61B 2017/00017* (2013.01);
(Continued)

(58) Field of Classification Search
CPC .... A61B 17/00234; A61B 2017/00022; A61B 2017/00115; A61B 2017/00119; A61B 2017/00123; A61B 2017/00128; A61B 2017/00221; A61B 2017/00292; A61B 2017/00296; A61B 2017/0034; A61B 2017/00345; A61B 2017/00353; A61B 2090/064; A61B 2090/065; A61B 34/76; G01L 5/226; G01L 5/228
See application file for complete search history.

(56) References Cited

U.S. PATENT DOCUMENTS 7,878,075 B2 * 2/2011 Johansson ............... B25J 13/084
73/862.046

* cited by examiner

*Primary Examiner* — Todd J Scherbel
(74) *Attorney, Agent, or Firm* — Muncy, Geissler, Olds & Lowe, P.C.

(57) ABSTRACT

Disclosed is a minimally invasive instrument with instant force feedback function, including a minimally invasive device, a sensing device, a computing device, and a warning device. The minimally invasive device may have an invasive portion, which may enter the human body to perform surgical operations. The sensing device is provided on the invasive portion of the minimally invasive device and may include a flexible conductive film, a plurality of bionic films and a plurality of liquid beads. The plurality of bionic films may be provided on a flexible conductive film. Each of the plurality of liquid beads may be covered by each of the plurality of bionic films. The computing device may be electrically connected to the flexible conductive film. The warning device may receive a warning signal and generate a warning message.

8 Claims, 4 Drawing Sheets

(51) Int. Cl.
  *A61B 17/00* (2006.01)
  *A61B 34/00* (2016.01)
  *G01L 5/22* (2006.01)
  *A61B 17/34* (2006.01)
  *A61B 17/04* (2006.01)
(52) U.S. Cl.
  CPC ............... *A61B 2017/00022* (2013.01); *A61B 2017/00026* (2013.01); *A61B 2017/00119* (2013.01); *A61B 2017/00221* (2013.01); *A61B 2090/064* (2016.02); *A61B 2090/065* (2016.02); *A61B 2090/0807* (2016.02)

MINIMALLY INVASIVE INSTRUMENT WITH INSTANT FORCE FEEDBACK FUNCTION

CROSS-REFERENCE TO RELATED APPLICATION

This application claims priority to and the benefit of Taiwan Patent Application No. 106124800, filed on Jul. 24, 2017, at the Taiwan Intellectual Property Office, the entire contents of which are herein incorporated by reference in their entirety.

BACKGROUND OF THE INVENTION

1. Field of the Invention

The present invention relates to a minimally invasive instrument with instant force feedback function. In particular, the present invention relates to a minimally invasive instrument that is combined with a technology for covering the liquid beads by the film to perform sense.

2. Description of the Related Art

Generally, when a doctor uses a minimally invasive equipment to perform a minimally invasive surgery, the minimally invasive instrument is controlled to penetrate into a human body through a trocar and used for the related surgical operations. It is more difficult for the doctor to perceive that the instruments are in contact with a non-target or the two instruments collide with each other unexpectedly during performing the surgical operations using the minimally invasive instrument without directly being in contact with the human body.

Furthermore, the minimally invasive surgery has become one of popular surgeries in the operating rooms of the current hospitals since the wounds are small and fast healed. On the other hand, the some hospitals currently have introduced DaVinci robots to perform the surgeries, but the doctors cannot obtain the situation of the minimally invasive instruments when using the mini-invasive surgery instruments or DaVinci robot arm that are instruments or robot arms without directly being in contact with the human body.

Therefore, there is a need for a minimally invasive instrument to improve the conventional problem described above.

SUMMARY OF THE INVENTION

In view of the above-mentioned problems of the conventional art, the object of the present invention is to provide a minimally invasive instrument with instant force feedback function, comprising a minimally invasive device, a sensing device, a computing device and a warning device. The minimally invasive device may have an invasive portion which may enter a human body to perform a surgical operation. The sensing device may be disposed on the invasive portion of the minimally invasive device, the sensing device may comprise a flexible conductive film, a plurality of bionic films and a plurality of liquid beads. The plurality of bionic films may be disposed on the flexible conductive film. Each of the plurality of liquid beads may be covered by each of the plurality of bionic films. The computing device may be electrically connected to the flexible conductive film, when at least one of the bionic films is in contact with the interior of the human body, the liquid bead is compressed by the bionic film to generate a pressure change on the flexible conductive film, the flexible conductive film converts the pressure change into a pressure electrical signal and transmits the pressure electrical signal to the computing device, and the computing device computes a pressure value based on the pressure electrical signal and transmits a warning signal when the pressure value is larger than a setting value, the warning device may receive the warning signal and generate a warning message.

Preferably, the bionic film may comprise parylene.

Preferably, the minimally invasive instrument with instant force feedback function of the present invention further comprises a communication device, which may be electrically connected to the computing device for receiving the pressure value and the warning signal.

Preferably, the communication device may be communicated with the computing device in a wireless manner.

Preferably, the communication device may be communicated with the warning device in a wireless manner.

Preferably, the minimally invasive device may comprise a gripping device, a cutting device, a stitching device, a stripping device, a puncturing device, a guiding device, a towing device and a staunching device.

Preferably, the warning device may further comprise a light-emitting element, which emits light when the warning device receives the warning message.

Based the above object, the present invention is also to provide a minimally invasive instrument with instant force feedback function, comprising a robot arm, a sensing device, a computing device and a warning device. The robot arm may control a minimally invasive device having an invasive portion, the invasive portion enters a human body to perform a surgical operation. The sensing device may be disposed on the invasive portion of the minimally invasive device, and comprise a flexible conductive film, a plurality of bionic films and a plurality of liquid beads. The plurality of bionic films may be disposed on the flexible conductive film. Each of the plurality of liquid beads is covered by each of the plurality of bionic films. The computing device electrically may be connected to the flexible conductive film, when at least one of the bionic films is in contact with the interior of the human body, the liquid bead is compressed by the bionic film to generate a pressure change on the flexible conductive film, the flexible conductive film converts the pressure change into a pressure electrical signal and transmits the pressure electrical signal to the computing device, and the computing device computes a pressure value based on the pressure electrical signal and transmits a warning signal when the pressure value is larger than a setting value. The warning device may receive the warning signal and generate a warning message.

Preferably, the minimally invasive device may comprise a gripping device, a cutting device, a stitching device, a stripping device, a puncturing device, a guiding device and a towing device.

Preferably, the computing device may transmit the warning signal to the robot arm and the robot arm may control the minimally invasive device stopping the surgical operation when the pressure value is larger than the setting value.

DETAILED DESCRIPTION OF THE PREFERRED EMBODIMENTS

For a better understanding of the features, contents and advantages of the present invention, and the effect that may be achieved therefrom, the present embodiments of the present invention are described in more detail as follows with reference to the accompanying drawings. It should be noted that the drawings and exemplary embodiments herein are used for the purpose of illustrating and explaining the present invention, without necessarily implying the actual ratio and the precise configuration. Therefore, in the accompanying drawings, the ratio and the configuration shall not be interpreted in any way that limits the scope of the present invention.

The embodiments of the minimally invasive instrument with instant force feedback function of the present invention is described with reference to the relative drawings as follows. For ease of understanding, the same elements in the following embodiments are represented by the same reference numbers.

Figure 1:
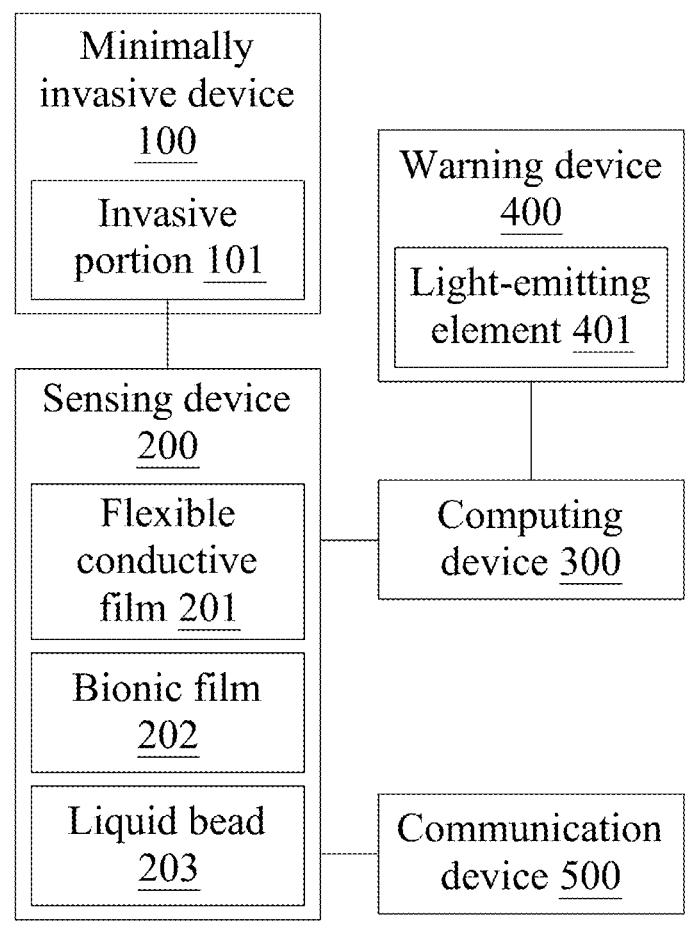
FIG. 1 is a first block diagram of a minimally invasive instrument with instant force feedback function according to an embodiment of the present invention.
Figure 2:
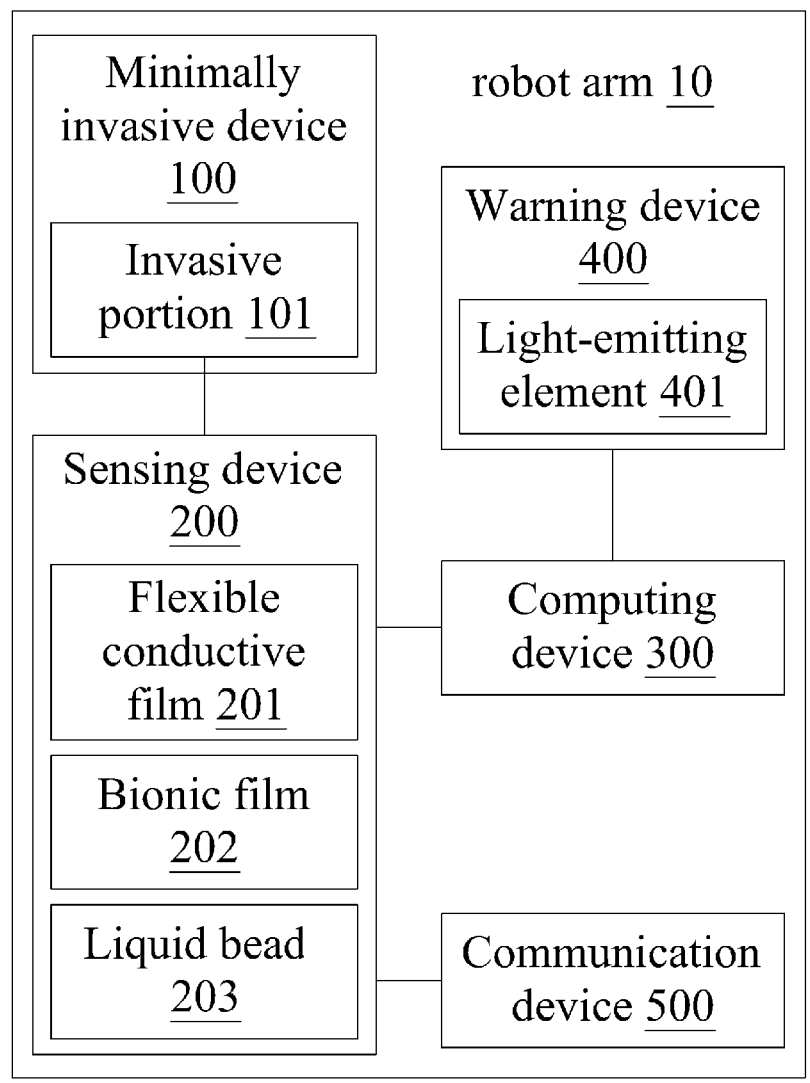
FIG. 2 is a second block diagram of a minimally invasive instrument with instant force feedback function according to an embodiment of the present invention.

Please refer to FIGS. 1 and 2, which are respectively a first block diagram of a minimally invasive instrument with instant force feedback function according to an embodiment of the present invention, and a second block diagram of a minimally invasive instrument with instant force feedback function according to the embodiment of the present invention.

As the two aspects of the minimally invasive instrument with instant force feedback function of the present invention, the first aspect may include a minimally invasive device 100, a sensing device 200, a computing device 300 and a warning device 400, the sensing device 200 disposed on the minimally invasive device 100 may sense an external environment and provide tactile sensing for the minimally invasive device 100, the warning device 400 prompts a user based on the sensing result calculated from the computing device 300.

The minimally invasive device 100 may have an invasive portion 101, which may enter a human body to perform a surgical operation, and the minimally invasive device 100 may comprise a gripping device, a cutting device, a stitching device, a stripping device, a puncturing device, a guiding device, a towing device and a staunching device.

The sensing device 200 may be disposed on the invasive portion 101 of the minimally invasive device 100 and comprise a flexible conductive film 201, a plurality of bionic films 202 and a plurality of liquid beads 203. The plurality of bionic films 202 may be disposed on the flexible conductive film 201, and each of the plurality of liquid beads 203 may be covered by each of the plurality of bionic films 202. In an embodiment, the bionic film 202 may comprise parylene, which may be used as an artificial crystal material and has good biocompatibility.

The computing device 300 may be electrically connected to the flexible conductive film 201, when at least one of the bionic films 202 is in contact with the interior of the human body, the liquid bead 203 is compressed by the bionic film 202 to generate a pressure change on the flexible conductive film 201, the flexible conductive film 201 converts the pressure change into a pressure electrical signal and transmits the pressure electrical signal to the computing device 300, and the computing device 300 computes a pressure value based on the pressure electrical signal and transmits a warning signal when the pressure value is larger than a setting value.

And then, the warning device 400 may receive a warning signal and generate a warning message, the warning device 400 may further comprise a light-emitting element 401, the light-emitting element 401 emits light when the warning device 400 receives a warning message, thereby prompts a user that the minimally invasive device 100 has been in contact with the interior of the human body.

In an embodiment, the present invention may further comprise a communication device 500 electrically connected to the computing device 300 for receiving the pressure value and the warning signal, and the communication device 500 may be communicated with the computing device 300 and the warning device 400 in a wireless manner, and thus the communication device 500 may be used to remotely transmit the pressure value sensed by the sensing device 200 to the computing device 300 and the warning device 400.

Further, as the second aspect of the minimally invasive instrument with instant force feedback function of the present invention, which comprises a robot arm 10, a sensing device 200, a computing device 300 and a warning device 400, the robot arm 10 may be a robot arm 10 as used in the DaVinci surgery and thus the robot arm 10 may be used for the surgery in the second aspect of the present invention.

As the second aspect of the present invention, the robot arm 10 may control the minimally invasive device 100 that may have an invasive portion 101, the invasive portion 101 may enters the interior of the human body to perform a surgery operation, the minimally invasive device 100 may comprise a gripping device, a cutting device, a stitching device, a stripping device, a puncturing device, a guiding device, a towing device and a staunching device.

The sensing device 200 may be disposed on the invasive portion 101 of the minimally invasive device 100 and may comprise a flexible conductive film 201, a plurality of bionic films 202 and a plurality of liquid beads 203. The plurality of bionic films 202 may be disposed on the flexible conductive film 201, and each of the plurality of liquid beads 203 may be covered by each of the plurality of bionic films 202. In an embodiment, the bionic film 202 may comprise parylene, which may be used as an artificial crystal material and have good biocompatibility.

The computing device 300 may be electrically connected to the flexible conductive film 201, when at least one of the bionic films 202 is in contact with the interior of the human body, the liquid bead 203 is compressed by the bionic film 202 to generate a pressure change on the flexible conductive film 201, the flexible conductive film 201 converts the pressure change into a pressure electrical signal and transmits the pressure electrical signal to the computing device 300, and the computing device 300 computes a pressure value based on the pressure electrical signal and transmits a warning signal when the pressure value is larger than a setting value.

And then, the warning device 400 may receive a warning signal and generate a warning message, the warning device 400 may further comprise a light-emitting element 401, the light-emitting element 401 emits light when the warning device 400 receives a warning message, thereby prompts a user that the minimally invasive device 100 has been in contact with the interior of the human body.

In an embodiment, when the pressure value is larger than a setting value, the computing device 300 may transmit a warning signal to the robot arm 10, and the robot arm 10 may control the minimally invasive device 100 stopping the surgical operation.

In another embodiment, as the first aspect of the present invention, the second aspect of the present invention also may further comprise a communication device 500 electrically connected to the computing device 300 for receiving the pressure value and the warning signal, and the communication device 500 may be communicated with the computing device 300 and the warning device 400 in a wireless manner, and thus the communication device 500 may be used to remotely transmit the pressure value sensed by the sensing device 200 to the computing device 300 and the warning device 400.

Figure 3:
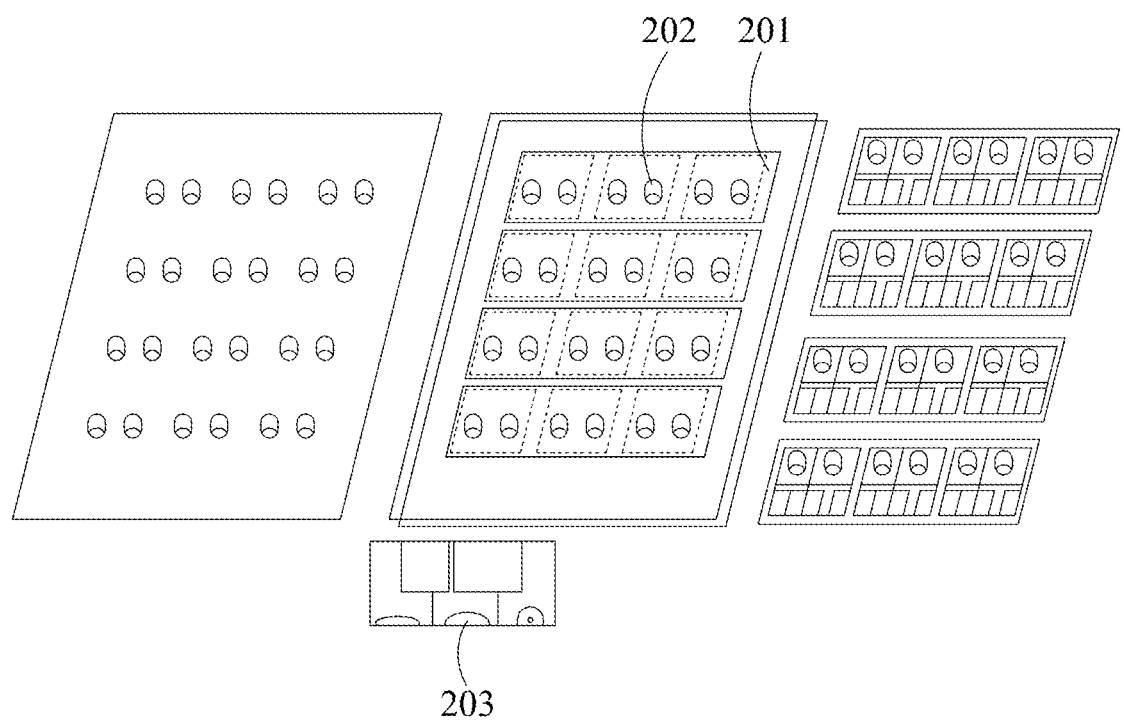
FIG. 3 is a schematic view of a sensing device of a minimally invasive instrument with instant force feedback function according to an embodiment of the present invention.
Figure 4:
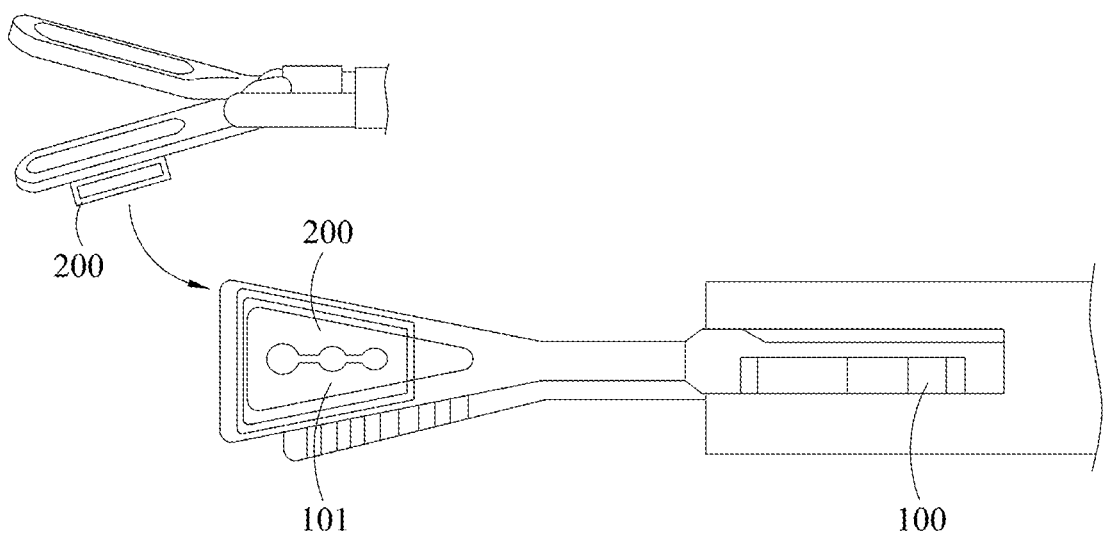
FIG. 4 is a schematic view of a minimally invasive instrument with instant force feedback function according to an embodiment of the present invention.

Please refer to FIGS. 3 and 4, which are respectively a schematic view of a sensing device of a minimally invasive instrument with instant force feedback function according to an embodiment of the present invention, and a schematic view of a minimally invasive instrument with instant force feedback function according to the embodiment of the present invention.

As shown in FIGS. 3 and 4, the plurality of bionic films 202 of the present invention cover the plurality of liquid beads 203 and may be disposed on the flexible conductive film 201, thus when the sensing device 200 is in contact with the interior of the human body, at least one of the bionic films 202 may compress the liquid bead 203, and then a pressure electrical signal is transmitted to the computing device 300 through the flexible conductive film 201. Therefore, the present invention also may use the computing device 300 to calculate the number of liquid beads 203 generating a pressure change on the flexible conductive film 201 when the sensing device 200 is in contact with the interior of the human body, and to calculate an actual contacting position based the position of the pressure change on the flexible conductive film 201.

In an embodiment, the present invention selects different kinds of the liquid beads 203 for different conditions, the liquid bead 203 may have different viscosity coefficients, for example, if the liquid bead 203 has a lower viscosity coefficient, the pressure change generated when the liquid bead 203 is compressed by the bionic film 202 is transferred more quickly due to the flow characteristics of the fluid.

In another embodiment, the sensing of the pressure change of the flexible conductive film 201 of the present invention may be performed in a resistive or capacitive sensing manner, if needed, the flexible conductive thin film 201 may be combined with the corresponding structures, for example, with the other suitable films, hard films and substrates etc. to achieve an effect in a resistive or capacitive sensing manner.

In an embodiment, as shown in FIG. 4, if the minimally invasive device 100 is a gripping device, the minimally invasive device 100 usually needs a trocar to perform the surgical operation, and may be in cooperation with the sensing device 200 to effectively provide a function of imitating tactile sense, it not only prompts the doctors, but also allows novice doctors can more quickly familiar with the minimally invasive surgery process.

The above-described embodiments are merely an exemplary illustration, and the present invention is not limited thereto. Any equivalent modification or change may be made thereto without departing from the scope and the spirit of the present invention and is covered by the appended claims.

What is claimed is:

1. A minimally invasive instrument with instant force feedback function, comprising:
    a minimally invasive device having an invasive portion which enters a human body to perform a surgical operation;
    a sensing device disposed on the invasive portion of the minimally invasive device, the sensing device comprises:
        a flexible conductive film;
        a plurality of bionic films disposed on the flexible conductive film; and
        a plurality of liquid beads each of which is covered by one of the plurality of bionic films;
    a computing device electrically connected to the flexible conductive film, when at least one of the bionic films is in contact with the interior of the human body, a liquid bead of the plurality of liquid beads is compressed by the at least one bionic film to generate a pressure change on the flexible conductive film, the flexible conductive film converts the pressure change into a pressure electrical signal and transmits the pressure electrical signal to the computing device, and the computing device computes a pressure value based on the pressure electrical signal and transmits a warning signal when the pressure value is larger than a setting value; and
    a warning device configured to receive the warning signal and generate a warning message.

2. The minimally invasive instrument with instant force feedback function of claim 1, wherein each bionic film comprises parylene.

3. The minimally invasive instrument with instant force feedback function of claim 1, further comprising a communication device, which is electrically connected to the computing device for receiving the pressure value and the warning signal.

4. The minimally invasive instrument with instant force feedback function of claim 3, wherein the communication device is communicated with the computing device in a wireless manner.

5. The minimally invasive instrument with instant force feedback function of claim 3, wherein the communication device is communicated with the warning device in a wireless manner.

6. The minimally invasive instrument with instant force feedback function of claim 1, wherein the warning device further comprises a light-emitting element, which emits light when the warning device receives the warning message.

7. A minimally invasive instrument with instant force feedback function, comprising:
    a minimally invasive device having an invasive portion which enters a human body to perform a surgical operation;
    a robot arm configured to control the minimally invasive device;
    a sensing device disposed on the invasive portion of the minimally invasive device, the sensing device comprises:
        a flexible conductive film;
        a plurality of bionic films disposed on the flexible conductive film; and a plurality of liquid beads each of which is covered by one of the plurality of bionic films;

a computing device electrically connected to the flexible conductive film, when at least one of the bionic films is in contact with the interior of the human body, a liquid bead of the plurality of liquid beads is compressed by the at least one bionic film to generate a pressure change on the flexible conductive film, the flexible conductive film converts the pressure change into a pressure electrical signal and transmits the pressure electrical signal to the computing device, and the computing device computes a pressure value based on the pressure electrical signal and transmits a warning signal when the pressure value is larger than a setting value; and a warning device configured to receive the warning signal and generate a warning message.

8. The minimally invasive instrument with instant force feedback function of claim 7, wherein the computing device transmits the warning signal to the robot arm and the robot arm controls the minimally invasive device stopping the surgical operation when the pressure value is larger than the setting value.

\* \* \* \* \*